(12) United States Patent
Horacek et al.

(10) Patent No.: US 7,229,599 B2
(45) Date of Patent: Jun. 12, 2007

(54) CHEMICAL DELIVERY CONTAINER

(75) Inventors: Jeffrey R. Horacek, Mentor, OH (US);
Christopher A. Jethrow, Maple Heights, OH (US)

(73) Assignee: Steris Inc., Temecula, CA (US)

( * ) Notice: Subject to any disclaimer, the term of this patent is extended or adjusted under 35 U.S.C. 154(b) by 361 days.

(21) Appl. No.: 10/632,992

(22) Filed: Aug. 1, 2003

(65) Prior Publication Data
US 2005/0025683 A1    Feb. 3, 2005

(51) Int. Cl.
*A61L 2/18* (2006.01)
(52) U.S. Cl. .................. 422/275; 422/278; 422/292
(58) Field of Classification Search ............ 422/275, 422/279, 266, 274; 206/221, 568; 68/17 R
See application file for complete search history.

(56) References Cited

U.S. PATENT DOCUMENTS

| | | | |
|---|---|---|---|
| 2,006,085 A * | 6/1935 | Lehmkuhl ................... 422/275 |
| 4,941,519 A | 7/1990 | Sestak et al. ................. 141/22 |
| 5,209,909 A | 5/1993 | Siegel et al. ................ 422/292 |
| 5,595,711 A | 1/1997 | Wilson et al. ............... 422/119 |
| 5,662,866 A | 9/1997 | Siegel et al. .................. 422/29 |
| 5,759,501 A * | 6/1998 | Livingston et al. .......... 422/275 |
| 5,858,305 A | 1/1999 | Malchesky .................... 422/28 |
| 5,863,499 A | 1/1999 | Kralovic ...................... 422/32 |
| 5,932,171 A | 8/1999 | Malchesky .................... 422/29 |
| 5,997,814 A | 12/1999 | Minerovic et al. ............ 422/29 |
| 6,158,580 A * | 12/2000 | Davis .......................... 206/204 |
| 6,325,968 B1 | 12/2001 | Fricker et al. ................. 422/28 |
| 6,482,358 B1 | 11/2002 | Kelsch et al. ................. 422/28 |

* cited by examiner

*Primary Examiner*—E. Leigh McKane
(74) *Attorney, Agent, or Firm*—Kusner & Jaffe; Michael A. Centanni

(57) ABSTRACT

A container for holding powdered reagents that interact with water to form an anti-microbial fluid for use in an apparatus for cleaning and microbially deactivating items. The container includes a fluid inlet connectable to a source of water on an apparatus for cleaning and microbially deactivating items and a fluid outlet in fluid communication with items to be microbially deactivated. A continuous fluid passage is defined through the container between the fluid inlet and the fluid outlet. A plurality of spaced-apart barrier elements are disposed within the fluid passage to define a plurality of isolated compartments within the container. The barrier elements are impervious to powdered reagents, but permeable to the chemical reagents when dissolved in a liquid. A first dry, powdered reagent is disposed within one of the compartments for forming an anti-microbial solution when water flows through the container.

19 Claims, 5 Drawing Sheets

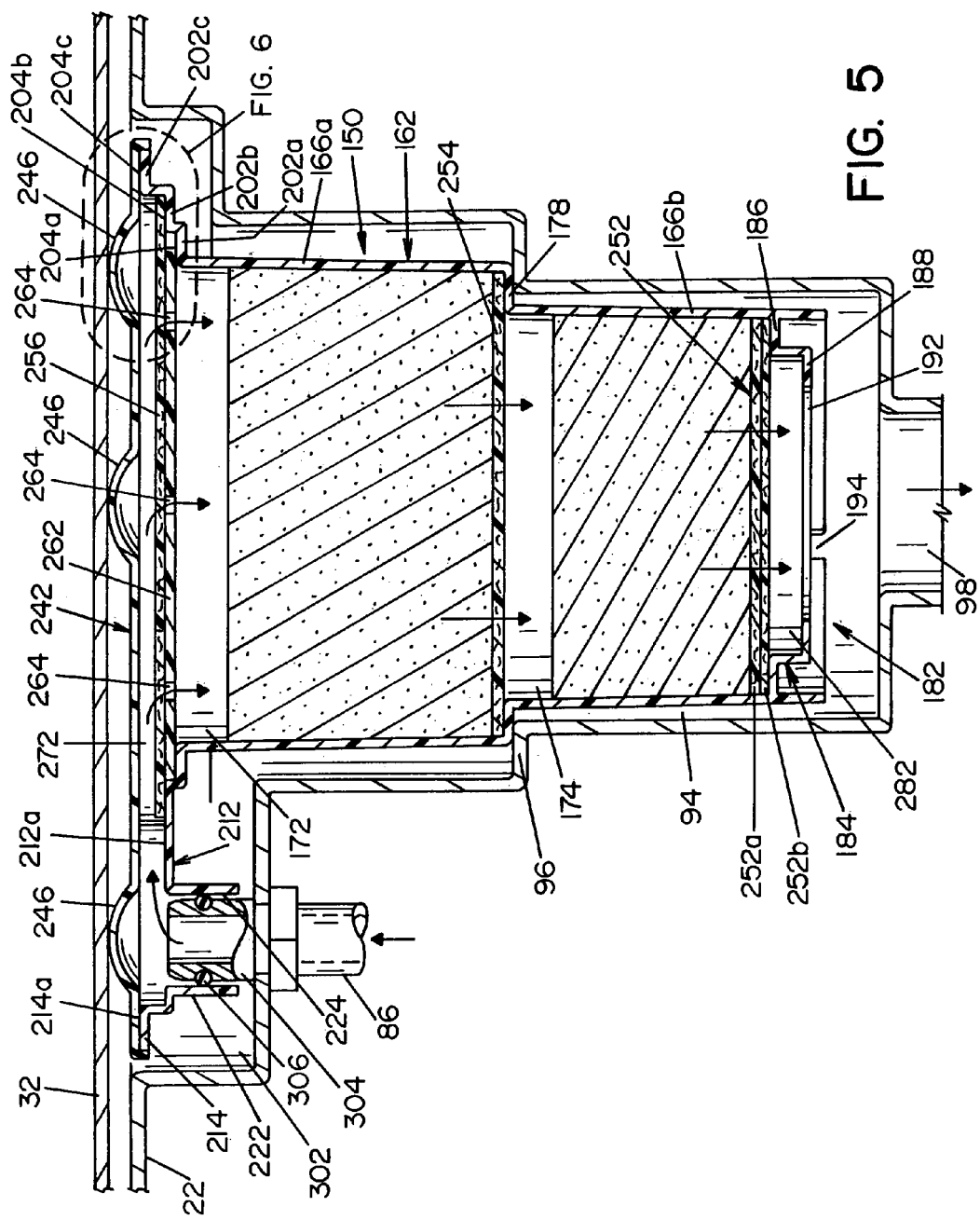

CHEMICAL DELIVERY CONTAINER

FIELD OF THE INVENTION

The present invention relates to disinfection or sterilization of medical, dental, pharmaceutical, veterinary or mortuary instruments and devices, and more particularly to a container for delivering chemistry to a processing chamber in a sterilization or disinfection system.

BACKGROUND OF THE INVENTION

Medical, dental, pharmaceutical, veterinary or mortuary instruments and devices that are exposed to blood or other body fluids require thorough cleaning and anti-microbial deactivation or sterilization between each use. Liquid microbial deactivation systems are now widely used to clean and deactivate instruments and devices that cannot withstand the high temperatures of a steam sterilization system. Liquid microbial deactivation systems typically operate by exposing the medical devices and/or instruments to a liquid disinfectant or sterilization composition, such as peracetic acid or some other strong oxidant.

In such systems, the instruments or devices to be cleaned are typically placed within a sterilization chamber within the liquid microbial deactivation system, or in a container that is placed within the sterilization chamber. A liquid disinfectant is then circulated through a liquid circulation system that includes the sterilization chamber (and the container therein) during a sterilization cycle.

The present invention provides a chemical delivery container for storing powdered reagents that are retained separately until used in a reprocessor.

SUMMARY OF THE INVENTION

In accordance with a preferred embodiment of the present invention, there is provided a container for holding powdered reagents that interact with water to for an anti-microbial fluid for use in an apparatus for cleaning and microbially deactivating items. The container is rigid and has a fluid inlet connectable to a source of water on an apparatus for cleaning and microbially deactivating items and a fluid outlet in fluid communication with items to be microbially deactivated. A continuous fluid passage is defined through the container between the fluid inlet and the fluid outlet. A plurality of spaced-apart barrier elements are disposed within the fluid passage to define a plurality of isolated compartments within the container. The barrier elements are impervious to powdered reagents, but permeable to the chemical reagents when dissolved in a liquid. A first dry, powdered reagent is disposed within one of the compartments for forming an anti-microbial solution when water flows through the container.

In accordance with another aspect of the present invention, there is provided an apparatus for microbially deactivating instruments and devices. The apparatus is comprised of a circulation system for selectively circulating water and an anti-microbial fluid through a chamber for holding instruments and devices to be microbially deactivated. The chamber forms a portion of the circulation system. A chemical delivery container is provided for holding powdered reagents that interact with water to form an anti-microbial fluid. The container has a plurality of compartments for holding the powdered chemical reagents. A continuous fluid passage extends through the container between a fluid inlet and a fluid outlet. The passage extends through the compartments. Porous barrier elements are disposed along the passage isolating one compartment from another compartment and isolating the compartments from the fluid inlet and the fluid outlet. The barrier elements are impervious to the powdered reagents, but permeable to the reagents when dissolved in water. A cavity in the apparatus receives the chemical delivery container. The cavity has a fluid line connectable to a source of water in communication with the cavity. The fluid line is connectable to the fluid inlet on the container when the container is disposed within the cavity, wherein water from the source of water may be forced into the container through the fluid inlet to interact with the chemical reagents in the container.

An advantage of the present invention is a chemical delivery container that facilitates material handling.

Another advantage of the present invention is a chemical delivery container that simplifies filling and sealing of two chemical reagents in separate compartments.

Another advantage of the present invention is a chemical delivery container that facilitates the handling and shipping of chemical reagents that interact with water to form an anti-microbial solution.

A still further advantage of the present invention is a chemical delivery container that promotes thorough mixing of chemical reagents and complete dissolving of the chemical reagents.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 5 is a sectional view of the chemical delivery container showing the container disposed within a recess in a reprocessor;

DETAILED DESCRIPTION OF PREFERRED EMBODIMENT

Figure 1:
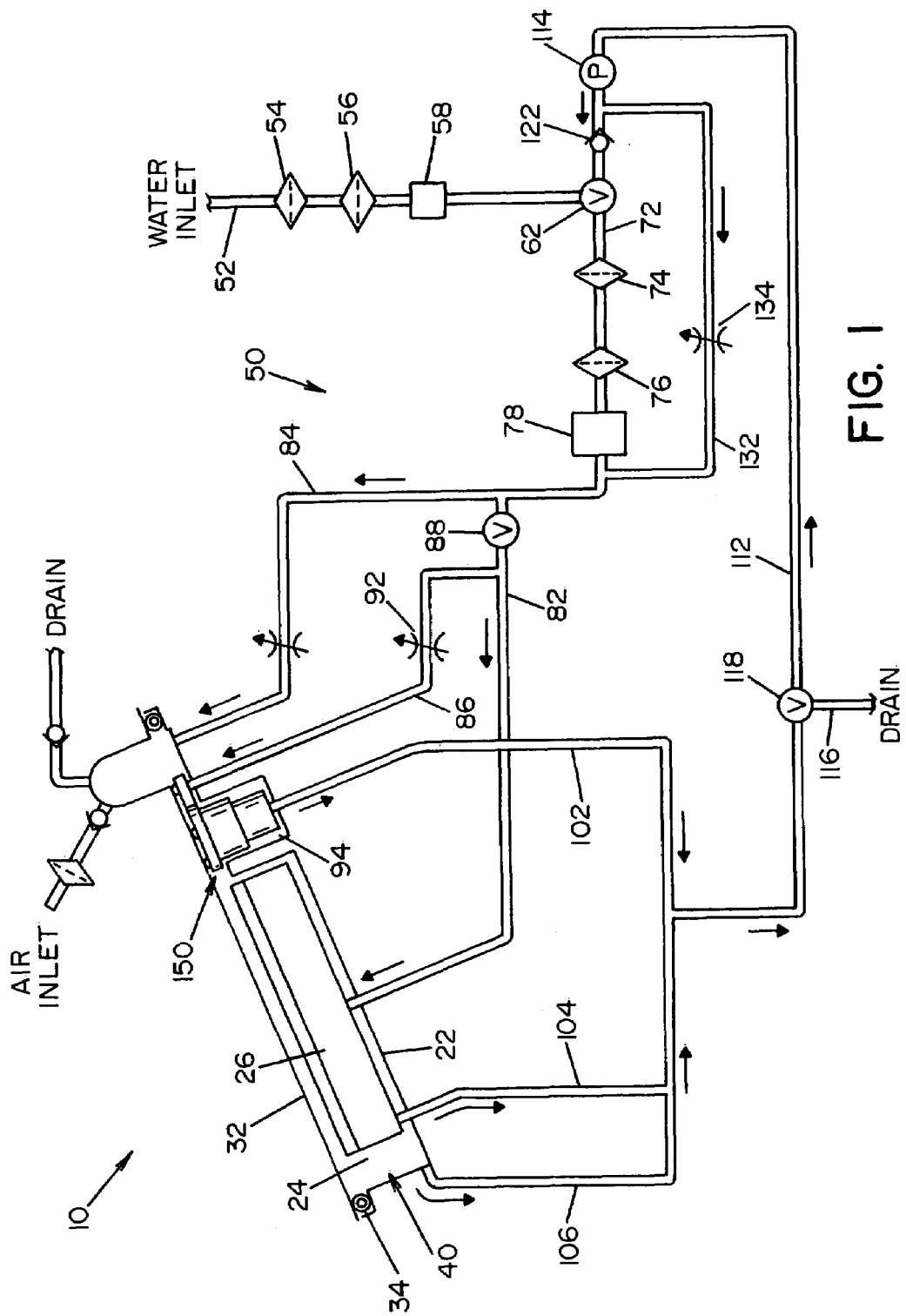
FIG. 1 is a schematic view of a microbial deactivation system.

Referring now to the drawings wherein the showings are for the purpose of illustrating a preferred embodiment of the invention only, and not for the purpose of limiting same, FIG. 1 shows a simplified, schematic piping diagram of a microbial deactivation apparatus 10 having a chemical delivery container 150, illustrating a preferred embodiment of the present invention.

Panel 22, that is part of a housing structure (not shown), defines a recess or cavity 24 dimensioned to receive items or instruments to be microbially deactivated. In the embodiment shown, a tray or container 26 is provided to receive the devices or instruments to be deactivated. Container 26 is dimensioned to be received within the recess or cavity 24, as illustrated in FIG. 1.

A manually operable lid 32 is movable between an opened position allowing access to cavity 24, and a closed position (shown in FIG. 1) closing or covering cavity 24. Seal element 34 surrounds cavity 24 and forms a fluid-tight-seal between lid 32 and panel 22 when lid 32 is in a closed position. Latch means (not shown) are provided for latching and securing lid 32 in a closed position during a deactivation cycle. Cavity 24 essentially defines a chamber 40 when lid 32 is in a closed position.

A fluid circulation system 50 provides the microbial deactivation fluid to chamber 40 and is further operable to circulate the microbial deactivation fluid through chamber 40. Fluid circulation system 50 includes water inlet line 52 that is connected to a source of heated water (not shown). A pair of macro filters 54, 56 are provided in water inlet lines 52 to filter large contaminants that may exist in the incoming water. An ultraviolet (UV) treatment device 58 for killing organisms within the water source is preferably provided in the inlet lines. A water valve 62 controls the flow of water from water inlet line 52 to a system feeder line 72. System feeder line 72 includes two micro filters 74, 76 in series to filter microscopic organisms and particles from the incoming water so as to provide sterile water to fluid circulation system 50. A fluid heating device 78 is disposed in feeder line 72 downstream of micro filters 74, 76. System feeder line 72 splits into first branch feeder line 82 and second branch feeder line 84. First branch feeder line 82 communicates with container 26 within chamber 40. Second branch feeder line 84 is connected to chamber 40 itself A secondary branch feeder line 86 splits off of first branch feeder line 82 and is directed to the inlet portion of a chemical delivery device 150 that contains dry chemical reagents that form the anti-microbial fluid used in apparatus 10. A valve 88 controls the flow through first branch feeder line 82 and through secondary branch feeder line 86 to chemical delivery device 150. A flow restrictor 92 is provided in secondary branch feeder line 86 to limit flow therethrough.

Chemical delivery device 150 is disposed within a well 94 formed within panel 22 of the housing structure. A branch return line 102 extends from chemical delivery device 150 and is connected to system return line 112. Likewise, branch fluid return lines 104, 106 extend from container 26 and chamber 40 respectively, and are connected to system return line 112. System return line 112 connects back with water inlet line 52 and fluid feeder line 72, as illustrated in FIG. 1. Pump 114 is disposed within system return line 112. Pump 114 is operable to circulate fluid through fluid circulation system 50. Drain line 116 is connected to system return line 112. Drain valve 118 controls fluid flow to the drain line 116. A directional check valve 122 is disposed in system feeder line 72 between water inlet line 52 and pump 114. A filter bypass line 132 communicates with system feeder line 72 on opposite sides of filters 74, 76. Specifically, one end of bypass line 132 is connected to system feeder line 72 between pump 114 and directional check valve 122. The other end of bypass line 132 communicates with system feeder line 72 beyond filters 74, 76 and heating device 78, but before where first and second branch feeder lines 82, 84 are formed. A flow restrictor 134 is provided in filter bypass line 132 to limit flow therethrough.

A system microprocessor (not shown) controls the operation of circulation system 50, as shall be described in greater detail below. The operation of circulation system 50 includes a microbial deactivation fluid generation phase, as shall also be described in greater detail below. An air inlet/fluid overflow assembly is provided at the uppermost portion of chamber 40 in fluid communication therewith. The air inlet/fluid overflow assembly includes an overflow drain to allow excess fluid within chamber 40 and circulation system 50 to overflow into a drain, and an air inlet to provide air into the chamber 40 to facilitate draining thereof A filter is provided in the air inlet to filter the incoming air.

Figure 2:
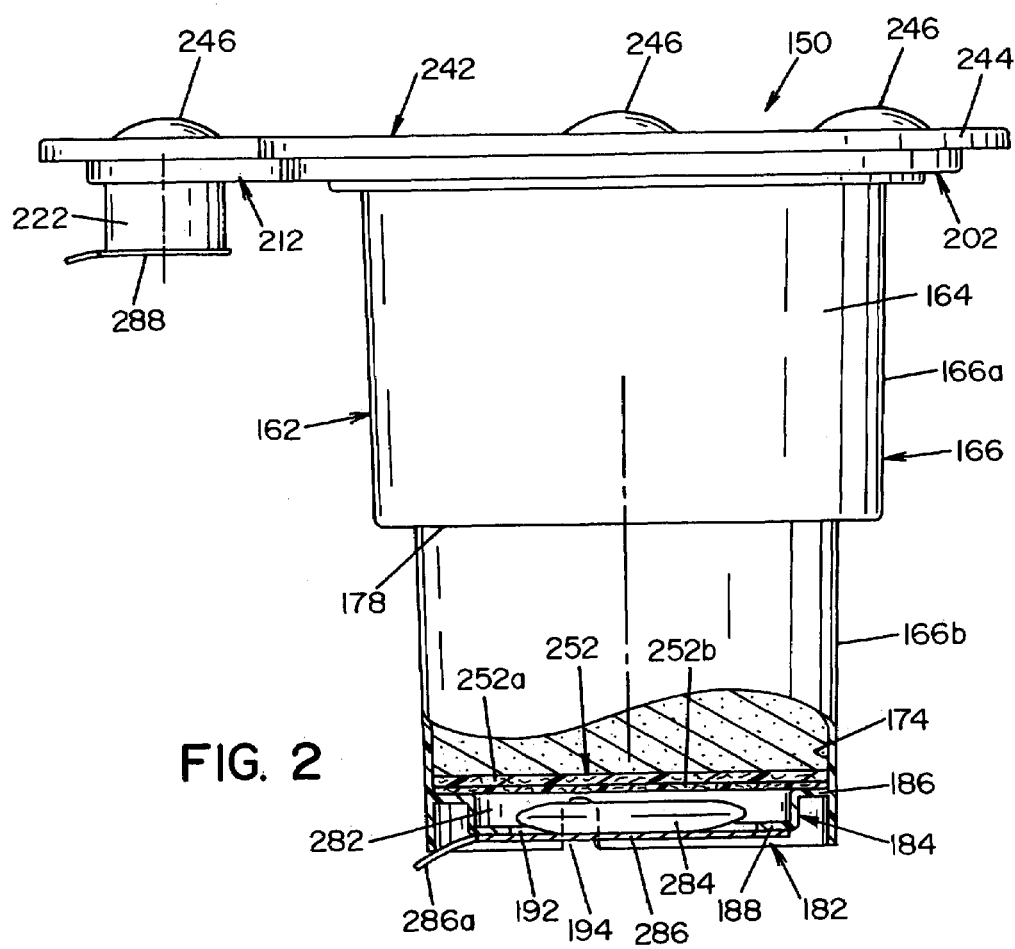
FIG. 2 is a partially sectioned, elevational view of a chemical delivery container used in a reprocessor, illustrating a preferred embodiment of the present invention.

As best seen in FIGS. 2 and 5, chemical delivery device 150 is basically comprised of a container 162 and a lid 242. In the embodiment shown, container 162 is generally cylindrical in shape and includes a tubular body 164 that is defined by an annular wall 166. Annular wall 166 includes a first wall section 166a that defines an upper container compartment 172 and a second wall section 166b that defines a lower container compartment 174. Container 162 is preferably formed of a molded plastic material, wherein annular wall 166 has a generally uniform thickness. As shown in the drawings, second wall section 166b is smaller in diameter than first wall section 166a. A flat, annular ledge or shoulder 178 is defined where first wall section 166a is joined to second wall section 166b.

The free end of second wall section 166b defines an opening 182. An annular stepped wall section 184 extends inwardly along the interior surface of second wall section 166b. Annular stepped wall section 184 is formed in the opening defined by second wall section 166b. Stepped wall section 184 defines a first annular surface 186 facing the interior of container 162 and a second annular surface 188 facing away from container 162. Stepped wall section 184 defines an opening 192.

As best seen in FIGS. 2 and 5, stepped wall section 184 is located within opening 182 defined by the end of second wall section 166b. A notch 194, best seen in phantom in FIG. 2, is formed in the end of second wall section 166b, where second wall section 166b extends beyond stepped wall section 166b.

Figure 6:
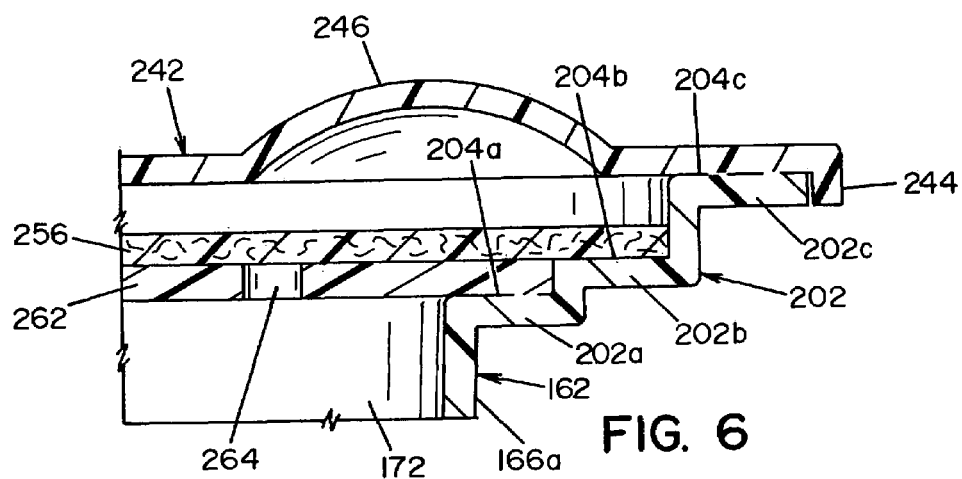
FIG. 6 is an enlarged view of the area identified in FIG. 5, showing a portion of the upper edge of the chemical delivery container.

Referring now to FIG. 6, at the upper end of chemical delivery device 150, first wall section 166a is formed into a stepped flange 202 that surrounds the opening defined by first wall section 166a. Flange 202 is comprised of three, offset flange sections (202a, 202b, 202c) that respectively define annular surfaces 204a, 204b, 204c that face outwardly away from the interior of container 162.

Figure 3:
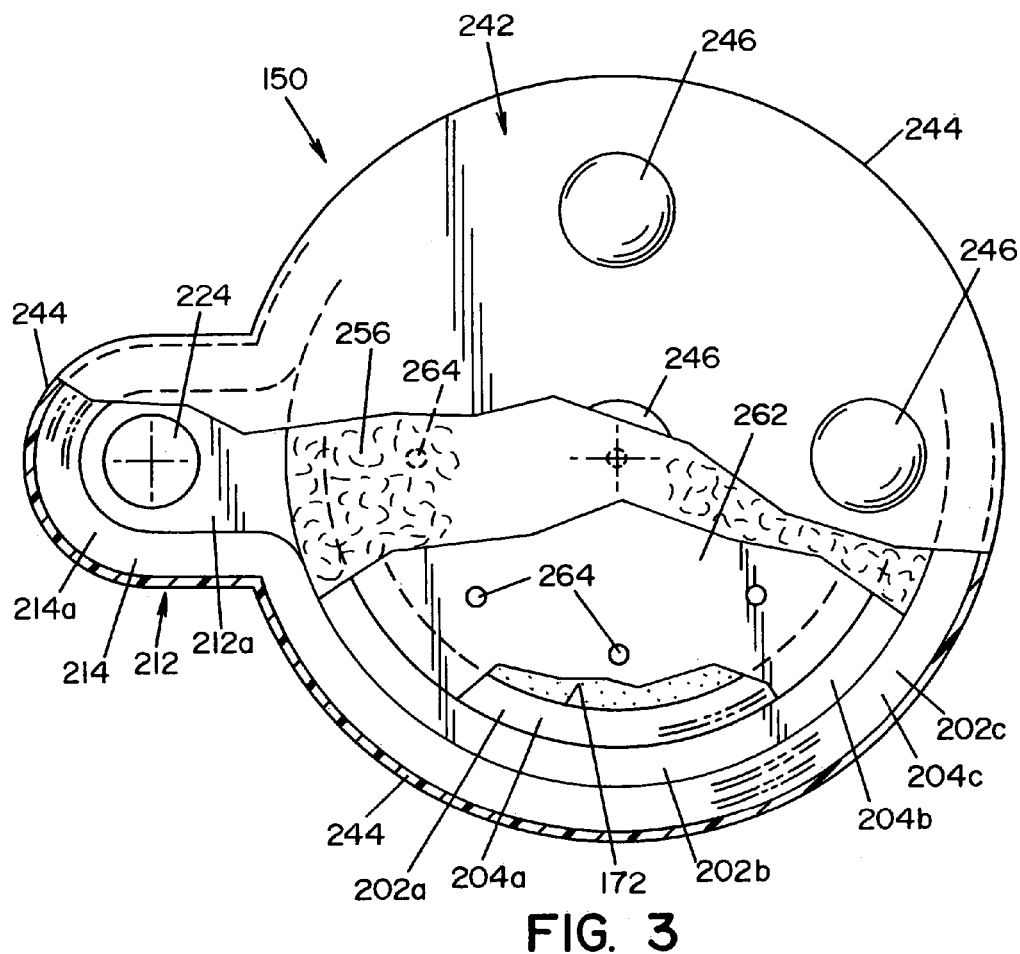
FIG. 3 is a partially sectioned, top plan view of the chemical delivery container shown in FIG. 2.

Stepped flange 202 is formed to have an extension 212, best seen in FIG. 3, projecting to one side of container 162. Extension 212 is generally U-shaped and has a planar surface 212a that is coplanar with annular surface 204b of section 202b of stepped flange 202. A flange section 214 is formed offset from surface 212a. Flange section 214 defines a surface 214a that lies in planar alignment, i.e., is coplanar with, annular surface 204c defined by flange section 202c.

Figure 4:
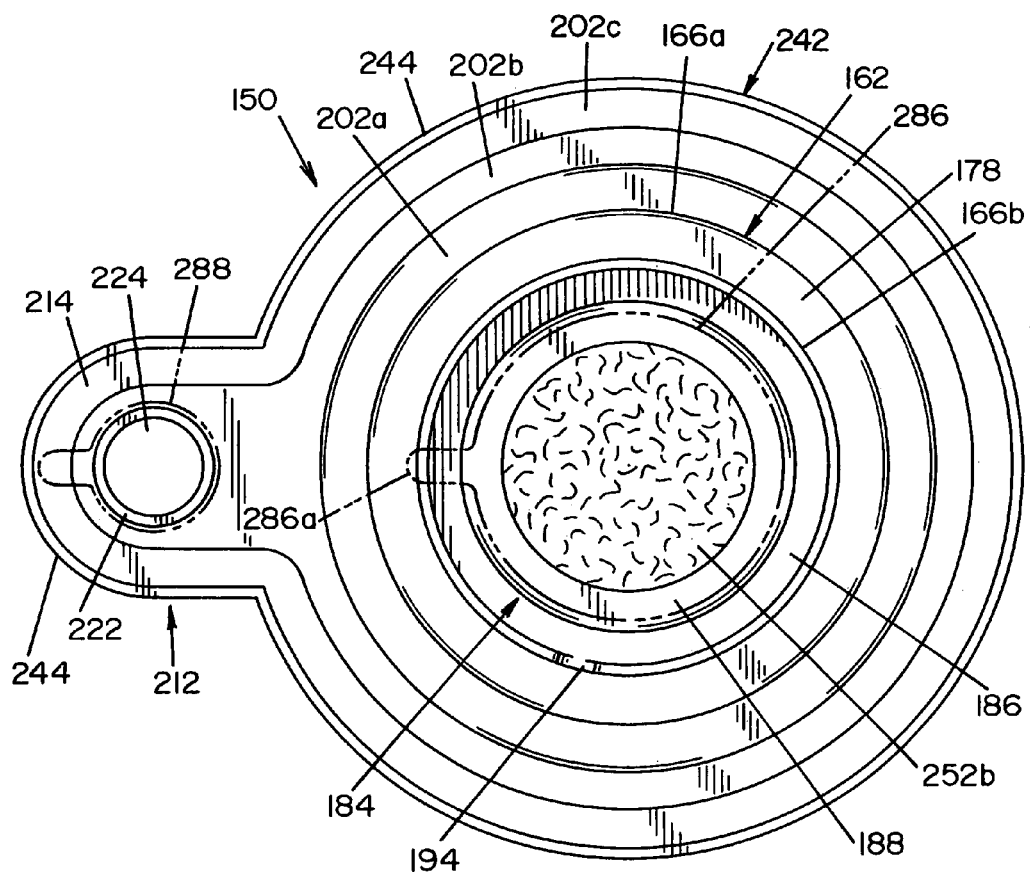
FIG. 4 is a bottom plan view of the chemical delivery container shown in FIG. 2.

A cylindrical pipe or nipple 222 extends from the lower surface of extension 212. Nipple 222 defines a cylindrical opening 224, best seen in FIGS. 3 and 4, that extends through surface 212a of extension 212.

Container 162 as heretofore described is preferably formed of a lightweight, rigid, polymer material, such as by way of example and not limitation, polypropylene.

Lid 242 is provided to cover and close the upper end of container 162. Lid 242 is basically a planar member shaped to conform to the shape of stepped flange 202 and extension 212 of container 162. Lid 242 includes a downwardly projecting lip 244 dimensioned to capture flange section 202c of stepped flange 202, as best seen in FIG. 6. Lid 242 includes a plurality of "bubbled" or "domed" portions 246, best seen in FIG. 6, that extends above the surface of lid 242.

A plurality of barrier elements 252, 254, 256, best seen in FIG. 5, are disposed within container 162 to define separate chambers or compartments within container 162. A first barrier element 252 is disposed at the bottom end of second wall section 166b to close opening 182 therethrough. Barrier element 252 is shaped to have an outer peripheral shape matching the inner profile of second wall section 166b. In the embodiment shown, barrier element 252 is circular in shape and is dimensioned to be snuggly received within second wall section 166b, wherein the peripheral edge of barrier element 252 rests on annular surface 186 of stepped wall section 184. Barrier element 252 is formed from a filter material that is impermeable to the dry reagents to be contained within chemical delivery device 150, but is permeable to water and to dissolved reagents.

In a preferred embodiment of the present invention, barrier element 252 includes a first filter layer 252a dimensioned to filter particles of a predetermined size, and a second filter layer 252b dimensioned to filter particles of a size smaller than that filtered by first filter layer 252a. In a preferred embodiment, first filter layer 252a is preferably dimensioned to filter particles of a size between 25 microns (μ) and 100 microns (μ), and more particularly, to filter particles of about 50 microns (μ). Second filter layer 252b is preferably dimensioned to filter particles of a size between 0.1 micron (μ) to 5 microns (μ). Suitable filter materials include polypropylene, polyethylene, nylon, rayon, rigid porous media, such as POREX™, expanded plastic, or other porous plastic, fabric, felt, mesh, and analogous materials. The filtering capabilities of the selected filtering material is related to the dry reagent contained within chemical delivery device 150. In a preferred embodiment, filter layers 252a, 252b are preferably formed of an ethylene-based polymer, such as polypropylene or polyethylene.

Barrier element 254 is dimensioned to snuggly fit within the opening defined by first wall section 166a and to be positioned on shoulder 178. Barrier element 256 is dimensioned to be positioned on annular surface 204b defined by section 202b of stepped flange 202, as best seen in FIG. 6. A support plate 262 having a plurality of spaced-apart apertures 264 is disposed below barrier element 256, as best seen in FIG. 6.

As best seen in FIG. 5, upper compartment 172 is defined within container 162 between barrier element 254 and barrier element 256. Lower compartment 174 is defined between barrier element 252 and barrier element 254. Lower compartment 174 is dimensioned to receive building chemicals, such as an acid precursor, preferably acetylsalicylic acid and a pre-salt, preferably sodium perborate. These two reagents are supplied at sufficient amounts to generate peracetic acid at a concentration of 1,500 ppm or better with the volume of water to be used in the system in which chemical delivery device 150 is to be used. The sodium perborate generates hydrogen peroxide, which, in combination with acetylsalicylic acid as an acetyl donor, forms peracetic acid.

The use of powdered reagents that react in a common solvent to generate chlorine gas, hydrogen peroxide, hypochlorous acid, hypochlorides, or other strong oxidants which have biocidal effects is also contemplated. Upper compartment 172 is dimensioned to receive various chemistries, such as buffers, inhibitors and wetting agents. Preferred copper and brass corrosion inhibitors include azoles, benzoates, and other five-member ring compounds, benzotriazoles, tolytriazoles, mercaptobenzothiazole, and the like. Other anti-corrosion buffering compounds include phosphates, molybdates, chromates, dichromates, tungstates, vanadates, and other borates, and combinations thereof. These compounds are effective for inhibiting steel and aluminum corrosion. For hard water in which calcium and magnesium salts may tend to precipitate, a sequestering reagent, such as sodium hexametaphosphate, is also included.

Figure 7:
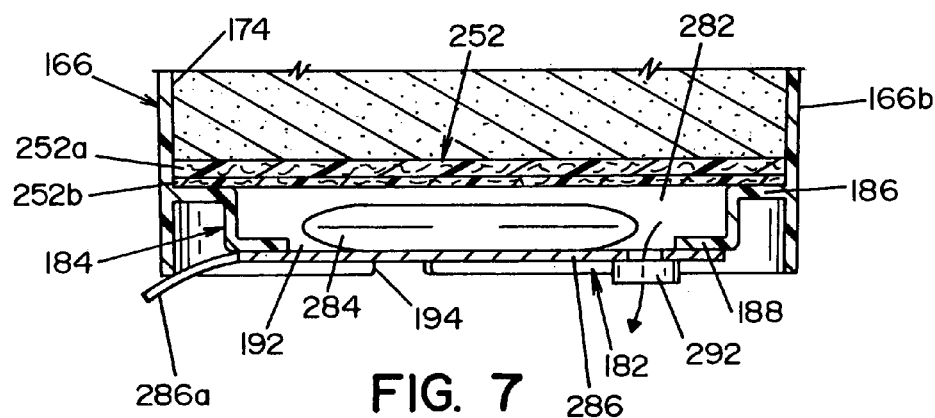
FIG. 7 is an enlarged, sectional view of the lower end of the chemical delivery container.

As best seen in FIG. 5, a fluid passage 272 is defined between barrier element 256 and lid 242. Passage 272 connects with opening 224 in nipple 222. At the other end of container 162, a small, annular compartment 282 is defined between barrier element 252 and stepped wall section 184. Compartment 282 is dimensioned to receive a desiccant packet 284, best seen in FIGS. 1 and 7. Compartment 282, with a desiccant packet 284 therein, is preferably sealed by a removable foil layer 286 applied onto annular surface 188 of stepped wall section 184. In the embodiment shown, foil layer 286 includes a tab 286a (shown in phantom in FIG. 4) to facilitate removal of foil layer 286 from container 162. Desiccant packet 284 is preferably attached to foil layer 286 by an adhesive (not shown) to allow removal of desiccant packet 284 when foil layer 286 is removed.

In an alternate embodiment of the invention, a purge valve 292 is provided in foil layer 286 (best seen in FIG. 7) to allow release of pressure that may build up within chemical delivery device 150. Foil layer 288 is also provided over opening 224 defined by nipple 222. It is contemplated that a directional check valve could be used within opening 224 of nipple 222 to restrict flow therethrough.

The present invention shall now be further described with reference to the assembly thereof. In this respect, the configuration of the present invention facilitates assembly of chemical delivery device 150 from the bottom up. An empty container 162, having foil layers 286, 288 attached thereto, is disposed in a vertical orientation, as shown in FIG. 1. Desiccant packet 284 is placed in compartment 282 through the opened, upper portion of container 162. As indicated above, packet 284 may be attached to foil layer 286 by an adhesive (not shown). With desiccant packet 284 in place, barrier element 252 is placed in lower container compartment 174 and pressed into place against annular surface 186 of stepped wall section 184. Barrier element 252, which is comprised of a polymer material, is ultrasonically welded to shoulder 178 of container 162.

A dry chemical reagent (of the type described above) is added to compartment 174. As indicated above, the chemical reagent in compartment 174 is comprised of an acid precursor, preferably acetylsalicylic acid and a pre-salt, but may also include wetting agents. When compartment 174 has been filled with the appropriate amount of dry chemical reagent, barrier element 254 is then placed into the upper container section and pressed onto ledge or shoulder 178. Barrier element 254 is then ultrasonically welded to ledge or shoulder 178. With barrier element 254 in place, a second, dry chemical reagent, namely a buffer that may include wetting agents is added to upper compartment 172. As indicated above, the chemical reagents added to upper compartment 172 are the chemical builders for forming the anti-microbial fluid.

When upper compartment 172 has been filled with the appropriate amount of dry reagent, support plate 262 is placed on annular surface 204a of section 202a of stepped flange 202. Barrier element 256 is then placed over plate 262, with the outer edges thereof resting on annular surface 204b of section 202b of stepped flange 202. The interior portion of barrier element 256 is supported by plate 262.

Lid 242 is then placed over the opened, upper end of container 162. Lip 244 of lid 242 and flange 202 of container 162 are then sealed by ultrasonic welding.

Referring now to FIG. 5, chemical delivery device 150 is adapted to be set into well 94 formed in chamber 40. In the embodiment shown, well 94 is generally cylindrical in shape and includes an annular ledge 96 on which chemical delivery device 150 may be set. Well 94 includes an opened port 98 at the bottom thereof that communicates with branch return line 102 of fluid circulation system 50 of reprocessor 10. Well 94 also includes a lateral cavity 302 dimensioned to receive extension 212 of chemical delivery device 150. Lateral cavity 302 includes a male fitting 304 that is formed through panel 22. Fitting 304 is connected to a branch feed line 86. Male fitting 304 is generally cylindrical in shape and includes an O-ring 306. Male fitting 304 is dimensioned to be received within opening 224 of nipple 222 on chemical delivery device 150 when chemical delivery device 150 is disposed within well 94.

Referring now to the operation of chemical delivery container 150, prior to initiation of a deactivation cycle, foil layers 286, 288 are removed from chemical delivery container 150. Desiccant package 284 is likewise removed from compartment 282 at the lower end of chemical delivery container 150. Chemical delivery container 150 is then inserted into well 94 of apparatus 10. Opening 224 in nipple 222 on extension 212 receives male fitting 304. O-ring 306 on male fitting 304 forms a generally fluid-tight seal between nipple 222 and male fitting 304. With container 26 inserted within chamber 40, lid 32 is closed and latched. As illustrated in FIG. 5, dome portion 246 of lid 242 is dimensioned to engage lid 32 thereby basically locking chemical delivery container 150 into place within well 94.

During a chemical generation and circulation phase, valve 88 and secondary branch line 86 is opened to force water into chemical delivery container 150 via male fitting 304. The water enters fluid passage 272 that is defined between lid 242 and barrier element 256. Since barrier elements 252, 254, 256 are permeable to fluids, the water enters into upper compartment 172, thereby mixing with the buffers and chemicals contained therein. The buffer solution penetrates through barrier element 254 into a lower compartment 174. The solution that passes from upper compartment 172 into lower compartment 174 mixes with the chemicals therein. The buffered acid solution then flows through lower barrier element 252. As indicated above, barrier element 252 is comprised of two layers, wherein the lowermost layer has a smart porosity wherein only completely dissolved chemicals may exit therefrom. The liquid anti-microbial solution then flows into branch return line 102 where it is circulated by circulation system 50 throughout the system, and more particularly, into chamber 40 and container 26.

The present invention thus provides a sealed container that does not require puncturing or spilling the chemical reagents into a fluid circulation line. Rather, water is forced along a fluid path between two open ends of container 150, thereby insuring proper mixing of respective reagents, and allowing only thoroughly mixed liquid to enter into circulation system 50 of microbial deactivation apparatus 10.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A chemical delivery device for holding powdered reagents that interact with water to form an anti-microbial fluid for use in an apparatus for cleaning and microbially deactivating items, comprised of:
   a rigid container having connection means defining a fluid inlet, said connection means being sealably connectable to a source of water on an apparatus for cleaning and microbially deactivating items and a fluid outlet in fluid communication with items to be microbially deactivated;
   a continuous fluid passage through said container between said fluid inlet and said fluid outlet;
   a plurality of spaced-apart barrier elements disposed within said fluid passage to define a plurality of isolated compartments within said container, said barrier elements being impervious to powdered reagents, but permeable to said chemical reagents when dissolved in a liquid;
   a dry, powdered reagent within said compartment for forming an anti-microbial solution when water flows through said container;
   a plate disposed in said fluid passage above said dry powdered reagent, said plate having a plurality of spaced-apart apertures formed therethrough; and
   a cavity defined above said plate, said cavity communicating with said fluid inlet, defining a portion of said continuous fluid passage, and being fluidly connected to said compartment by said plurality of spaced-apart apertures formed through said plate.

2. A chemical delivery device as defined in claim 1, wherein said container is formed of a molded polymer material.

3. A chemical delivery device as defined in claim 2, wherein said barrier elements are formed of a porous polymer material.

4. A chemical delivery device as defined in claim 3, wherein said barrier elements are formed of an ethylene-based polymer.

5. A chemical delivery device as defined in claim 3, wherein said barrier elements are size exclusive filters.

6. A chemical delivery device as defined in claim 5, wherein said barrier element adjacent said fluid outlet includes a microbial filter layer that filters particles having a size of 0.1µ or greater from fluid passing through said container.

7. A chemical delivery device as defined in claim 1, further comprising a removable, moisture barrier covering said fluid inlet and said fluid outlet.

8. A chemical delivery device as defined in claim 7, further comprising a removable desiccant material in said passage.

9. A chemical delivery device as defined in claim 8, wherein said desiccant material is in said passage at said fluid outlet.

10. A chemical delivery device as defined in claim 1, wherein said container is generally cylindrical in shape.

11. A chemical delivery device as defined in claim 1, wherein said container has two compartments and one of said compartments holds an acid precursor.

12. A chemical delivery device as defined in claim 11, wherein said acid precursor includes acetylsalicylic acid.

13. A chemical delivery device as defined in claim 1, wherein said container includes a first compartment disposed between said fluid inlet and said fluid outlet, and a second compartment disposed between said first compartment and said fluid outlet, said first compartment containing said dry reagent and said second compartment containing a second dry reagent.

14. An apparatus for microbially deactivating instruments and devices, said apparatus comprised of:
a circulation system for selectively circulating water and an anti-microbial fluid through a chamber for holding instruments and devices to be microbially deactivated, said chamber forming a portion of said circulation system;
a chemical delivery device for holding powdered chemical reagents that interact with water to form an anti-microbial fluid, said chemical delivery device having:
connection means defining a fluid inlet, said connection means being sealably connectable to said circulation system;
a fluid outlet in communication with said chamber;
a plurality of compartments for holding said powdered chemical reagents,
a continuous fluid passage extending through said chemical delivery device between said fluid inlet and said fluid outlet, said passage extending through said compartments,
porous barrier elements disposed along said passage isolating one compartment from another compartment and isolating said compartments from said fluid inlet and said fluid outlet, said barrier elements being impervious to said powdered reagents, but permeable to said reagents when dissolved in water;
a plate disposed above said powdered chemical reagents within said fluid passage, said plate having a plurality of spaced-apart apertures communicating with said chemical reagents;
a space defined above said plate, said space communicating with said fluid inlet, defining a portion of said continuous fluid passage, and being fluidly connected to said compartment by said plurality of spaced-apart apertures formed through said plate; and
a cavity in said apparatus for receiving said chemical delivery device, said cavity having a fluid line connectable to a source of water in communication with said cavity, said fluid line being sealably connectable to said fluid inlet on said chemical delivery device when said chemical delivery device is disposed within said cavity, wherein water from said source of water may be forced into said device through said fluid inlet to interact with said chemical reagents in said device.

15. An apparatus for microbially deactivating instruments and devices as defined in claim 14, wherein said spaced-apart apertures of said plate are disposed radially around a central portion of said plate.

16. An apparatus for microbially deactivating instruments and devices as defined in claim 14, further comprising:
porous barrier elements disposed along said passage isolating one compartment from another compartment and isolating said plurality of compartments from said fluid inlet and said fluid outlet, said barrier elements being impervious to said powdered reagents, but permeable to said reagents when dissolved in water.

17. A chemical delivery device for holding powdered reagents that interact with water to form an anti-microbial fluid for use in an apparatus for cleaning and microbially deactivating items, comprised of:
a rigid container having a connection means defining a fluid inlet that is sealably connectable to a source of water on an apparatus for cleaning and microbially deactivating items and a fluid outlet in fluid communication with items to be microbially deactivated;
a continuous fluid passage through said container between said fluid inlet and said fluid outlet;
a plate disposed in said fluid passage, said plate having a plurality of spaced-apart apertures formed therethrough;
a rigid lid disposed above said plate;
a plurality of spaced-apart barrier elements disposed within said fluid passage to define a plurality of isolated compartments within said container, each of said barrier elements being impervious to powdered reagents, but permeable to said chemical reagents when dissolved in a liquid; said compartments defined within said container below said plate;
a dry, powdered reagent within said compartment for forming an anti-microbial solution when water flows through said container;
a cavity defined between said plate and said lid, said cavity being isolated from said compartments by said plate, and said cavity being fluidly connected to said compartment by said plurality of spaced-apart apertures formed through said plate.

18. A chemical delivery device as defined in claim 17, wherein said barrier elements are size exclusive filters.

19. A chemical delivery device as defined in claim 17, wherein said container has two compartments and one of said compartments holds an acid precursor.

* * * * *